(12) United States Patent
Ikushima

(10) Patent No.: US 9,638,580 B2
(45) Date of Patent: May 2, 2017

(54) DEVICE FOR MEASURING HEAT RADIATION OF OBJECT TO BE MEASURED, METHOD FOR MEASURING HEAT RADIATION OF OBJECT TO BE MEASURED, AND CELL FOR MEASURING HEAT RADIATION

(71) Applicant: TOKYO UNIVERSITY OF AGRICULTURE AND TECHNOLOGY, Tokyo (JP)

(72) Inventor: Kenji Ikushima, Tokyo (JP)

(73) Assignee: Tokyo University of Agriculture and Technology, Tokyo (JP)

( * ) Notice: Subject to any disclaimer, the term of this patent is extended or adjusted under 35 U.S.C. 154(b) by 135 days.

(21) Appl. No.: 14/380,167

(22) PCT Filed: Feb. 20, 2013

(86) PCT No.: PCT/JP2013/054151
§ 371 (c)(1),
(2) Date: Aug. 21, 2014

(87) PCT Pub. No.: WO2013/125571
PCT Pub. Date: Aug. 29, 2013

(65) Prior Publication Data
US 2015/0014540 A1    Jan. 15, 2015

(30) Foreign Application Priority Data
Feb. 24, 2012   (JP) .................................. 2012-038747

(51) Int. Cl.
*G01J 5/02*    (2006.01)
*G01J 5/08*    (2006.01)
(Continued)

(52) U.S. Cl.
CPC ........... *G01J 5/0806* (2013.01); *G01J 5/0037* (2013.01); *G01J 5/0205* (2013.01); *G01J 5/0275* (2013.01);
(Continued)

(58) Field of Classification Search
CPC ..................................................... G01J 5/0806
(Continued)

(56) References Cited

U.S. PATENT DOCUMENTS 5,390,023 A * 2/1995 Biegen ...................... G01B 9/04
356/497
6,381,013 B1 * 4/2002 Richardson ............. H01J 37/20
356/305

(Continued)

FOREIGN PATENT DOCUMENTS

| JP | 3760196 B2 | 1/2006 |
| JP | 2008-170969 A | 7/2008 |
| JP | 2009-300841 A | 12/2009 |

OTHER PUBLICATIONS

Iguchi et al., "Micro Thermography with a Solid Immersion Lens," *Abstracts of the Meeting of the Physical Society of Japan* 66(1):731, 25aHA-47, Mar. 3, 2011 (3 pages)(English translation provided).
(Continued)

*Primary Examiner* — Edwin Gunberg
(74) *Attorney, Agent, or Firm* — Seed IP Law Group, LLP

(57) ABSTRACT

An apparatus 100 for measuring thermal radiation in one mode of the present invention is used for detecting thermal radiation of an object 12 to be measured. The apparatus 100 is provided with: a sample cell 10 which includes the object 12 to be measured which is a liquid or an object containing liquid, and a housing part which houses the object 12 to be measured and includes one wall formed of a base 16
(Continued)

transmitting a wavelength of the thermal radiation; a first lens 20 formed by partially cutting a sphere so that a cross section forms a plane, wherein the sample cell 10 is arranged so that, when the base 16 is in close contact with the plane of the first lens 20, focus of a second lens is placed on at least a part of the object 12 to be measured, for example, located on the base 16, the second lens including the first lens 20 and the base 16 and used for detecting the thermal radiation through the first lens 20; a position controller 60 which controls one of the object 12 to be measured and the first lens 20 so as to be able to abut on and separate from the other in an optical axis direction; a vibrational controller 40 which allows one of the object to be measured and the first lens to vibrate with respect to the other and controls a frequency of the vibration; and a detector 70 which detects the thermal radiation through the first lens 20.

17 Claims, 6 Drawing Sheets

(51) Int. Cl.

| | | |
|---|---|---|
| *G02B 13/14* | (2006.01) | |
| *G02B 13/24* | (2006.01) | |
| *G01J 5/00* | (2006.01) | |
| *G01J 5/06* | (2006.01) | |
| *G01N 1/28* | (2006.01) | |
| *G01N 21/03* | (2006.01) | |

(52) U.S. Cl.
CPC .............. *G01J 5/06* (2013.01); *G01N 1/286* (2013.01); *G01N 21/03* (2013.01); *G02B 13/14* (2013.01); *G02B 13/24* (2013.01); *G01J 2005/0059* (2013.01); *G01J 2005/0077* (2013.01); *G01J 2005/0081* (2013.01); *G01N 2001/2873* (2013.01); *G01N 2201/068* (2013.01)

(58) Field of Classification Search
USPC .................................................. 359/356, 357
See application file for complete search history.

(56) References Cited

U.S. PATENT DOCUMENTS

| | | | | |
|---|---|---|---|---|
| 6,831,013 | B2 * | 12/2004 | Tsai .................. | H01L 21/76813 257/E21.035 |
| 7,042,647 | B2 * | 5/2006 | Lo ...................... | G01N 21/8806 250/216 |
| 2005/0254121 | A1 | 11/2005 | Komiyama et al. | |
| 2008/0149867 | A1 | 6/2008 | Konishi et al. | |
| 2012/0176673 | A1 * | 7/2012 | Cooper .................. | G02B 21/16 359/386 |

OTHER PUBLICATIONS

Kobayashi et al., "Solution Thermography with a Solid Immersion Lens," *Extended Abstracts, Japan Society of Applied Physics and Related Societies* (CD-ROM), vol. 59, 17A-B11-5, Feb. 29, 2012 (3 pages)(English translation provided).

International Search Report for PCT/JP2013/054151, mailed Apr. 9, 2013 (4 pages).

* cited by examiner (b)

DEVICE FOR MEASURING HEAT RADIATION OF OBJECT TO BE MEASURED, METHOD FOR MEASURING HEAT RADIATION OF OBJECT TO BE MEASURED, AND CELL FOR MEASURING HEAT RADIATION

TECHNICAL FIELD

The present invention relates to an apparatus for measuring thermal radiation of an object to be measured, a method for measuring thermal radiation of an object to be measured, and a sample cell for measuring thermal radiation.

BACKGROUND ART

The inventor of this application and others have proceeded research on a technique for measuring thermal radiation using infrared light and the measurement technique has been disclosed (Non-Patent Document 1). The inventor of this application and others have disclosed a so-called passive infrared light condensing apparatus which combines a solid immersion lens and an atomic force microscopy (AFM) (Patent Document 1). However, the above techniques are each mainly based on the condition that an object to be measured is a solid material.

PRIOR ART DOCUMENTS

Patent Document

Patent Document 1: Japanese Patent No. 3760196

Non-Patent Document

Non Patent Document 1: IKUSHIMA et al., "Micro Thermography with a Solid Immersion Lens", Abstracts of the Meeting of the Physical Society of Japan, 03 Mar. 2011, vol. 66 (1), Issue 4, page 731

SUMMARY OF THE INVENTION

Problems to be Solved by the Invention

The space resolution of a commercially available passive infrared microscope (a thermography microscope, for example) is determined depending on the diffraction limit in the atmosphere or the size of an array sensor. Therefore, a commercially available passive infrared microscope cannot achieve high space resolution. Further, as described above, the techniques that have been obtained by research and development up to now use a solid material as an object to be measured. Therefore, when the object to be measured is a liquid or an object containing liquid, it is difficult to apply the conventional techniques without change. In particular, when measuring thermal radiation of a liquid or an object containing liquid, it is only possible to obtain information about the temperature of the surface of the liquid or the object containing liquid cooled by the heat of vaporization. Therefore, it is not possible to acquire original accurate information about heat generation of the object to be measured. Further, when the object to be measured is an extremely minute object (a cell, for example), the radiation intensity decreases in proportion to the radiation area. Therefore, it is extremely difficult to demand high space resolution by a so-called passive method. Further, for example, in order to achieve observation of the movement inside a biomolecule or temperature imaging inside a cell, a technique for further accurately distinguishing so-called background radiation that inevitably occurs in a measurement system and a target signal (thermal radiation) from an object to be measured is required.

In addition, when employing a conventional measurement method that uses infrared light, strong external light is applied during the measurement. Therefore, for example, when an object to be measured is a biomolecule or a cell, the object to be measured is disadvantageously excited by the external light. As a result, it becomes extremely difficult to detect a faint target signal from the objet to be measured itself.

Therefore, when an object to be measured is a liquid or an object containing liquid, there are still not a few technical problems in improving the space solution and distinguishing background radiation and a target signal (thermal radiation) from each other. In particular, achieving high space resolution by a passive method that does not use application of infrared light or the like from the outside leads to creating strong demand in the various industrial worlds and medical world.

Solutions to the Problems

The present invention solves at least one of the above problems to thereby achieve exhibition of high space resolution and/or accurate distinction between background radiation and a target signal when an object to be measured is a liquid or an object containing liquid, and greatly contributes to the development of a technique for measuring thermal radiation of an object to be measured.

The inventor of this application has performed creative research and analysis for solving the above technical problems. As a result, it has been confirmed that it is possible to exhibit high space resolution and, at the same time, accurately distinguish background radiation and a target signal from each other without performing irradiation from the outside by exercising a special ingenuity for skillfully controlling the relationship between an object to be measured which is a liquid or an object containing liquid and a lens in which the cross section obtained by partially cutting a sphere forms a plane in the measurement. Further, the inventor of this application has found out that utilizing interference light between the object to be measured and the lens makes it easy to adjust the parallelism with respect to the lens and the distance from the lens required in actual measurement for achieving high space resolution and accurate extraction of a target signal. The present invention has been made based on such knowledge.

An apparatus for measuring thermal radiation of an object to be measured according to an aspect of the present invention is used for detecting thermal radiation of an object to be measured. Specifically, the apparatus for measuring thermal radiation is provided with: a sample cell including the object to be measured which is a liquid or an object containing liquid and a housing part housing the object to be measured and including one wall formed of a base transmitting a wavelength of the thermal radiation; and a first lens formed by partially cutting a sphere so that a cross section forms a plane, wherein the sample cell is arranged so that, when the base is in close contact with the plane of the first lens, the focus of a second lens is placed on at least a part of the object to be measured located on the base or close to the base, the second lens including the first lens and the base and used for detecting the thermal radiation through the first lens. In addition, the apparatus for measuring thermal radiation is provided with: a position controller which controls one of the object to be measured and the first lens so as to be able to abut on and separate from the other in an optical axis direction; a vibrational controller which allows one of the object to be measured and the first lens to vibrate with respect to the other and controls a frequency of the vibration; and a detector which detects the thermal radiation through the first lens.

In the apparatus for measuring thermal radiation, the sample cell is arranged so that, when the base in the sample cell is in close contact with the plane of the first lens (an objective lens, for example) formed by partially cutting a sphere so that the cross section forms the plane, the focus of the second lens (including the first lens and the base) for detecting the thermal radiation through the first lens is placed on at least a part of the object to be measured. A typical example will be described. When the plane of the first lens formed by partially cutting a sphere so that the cross section forms the plane and the base in the sample cell are in close contact with each other, a function as a solid immersion lens (an example of the second lens) is exhibited. Therefore, in the apparatus for measuring thermal radiation, thermal radiation of a liquid or an object containing liquid is measured not at the liquid-gas interface, but at the liquid-solid interface. As a result, it is possible to suppress a cooling effect obtained by the heat of vaporization from the object to be measured. In addition, the apparatus for measuring thermal radiation is further provided with the position controller which controls one of the object to be measured and the first lens so as to be able to abut on and separate from the other in the optical axis direction and a vibrational controller which allows one of the object to be measured and the first lens to vibrate with respect to the other and controls the frequency of the vibration. Therefore, for example, a signal of thermal radiation (typically, a signal of infrared light) can be measured as a function of the distance between the base in the sample cell and the plane in the first lens. As a result, it becomes possible to observe interference phenomena of infrared light between the base and the plane in the first lens in a condition capable of distinguishing the background radiation and the target signal (thermal radiation) from each other. Further, as described above, in the apparatus for measuring thermal radiation, the base in combination with the first lens exhibits a function as a solid immersion lens (an example of the second lens). Therefore, it is possible to utilize at least a wavelength that is shorter than a wavelength propagating in vacuum or the atmosphere, and therefore improve the space resolution.

Further, in order to prevent unnecessary attenuation of a signal to be measured and exhibit high space resolution, it is preferred that the base and the first lens be each made of a material having a small absorption coefficient and a large dielectric constant in addition to the above configuration of the apparatus for measuring thermal radiation. Further, design that achieves substantially no spherical aberration when the plane of the first lens formed by partially cutting a sphere so that the cross section forms the plane and the base in the sample cell are in close contact with each other (hereinafter, also referred to as "aplanatic design") further improves the space resolution.

Further, a method for measuring thermal radiation of an object to be measured according to an aspect of the present invention is performed for detecting thermal radiation of an object to be measured. Specifically, the method for measuring thermal radiation uses a sample cell which includes the object to be measured which is a liquid or an object containing liquid and a housing part housing the object to be measured and including one wall formed of a base transmitting a wavelength of the thermal radiation, and is arranged so that, when the base is in close contact with a plane of a first lens formed by partially cutting a sphere so that the cross section forms the plane, the focus of a second lens is placed on at least a part of the object to be measured located on the base or close to the base, the second lens including the first lens and the base and used for detecting the thermal radiation through the first lens. In addition, the method for measuring thermal radiation detects the thermal radiation through the first lens by allowing one of the object to be measured and the first lens to abut on or separate from the other in the optical axis direction and allowing one of the object to be measured and the first lens to vibrate with respect to the other.

In the method for measuring thermal radiation, the sample cell is used so that, when the base in the sample cell is in close contact with the plane of the first lens (an objective lens, for example) formed by partially cutting a sphere so that the cross section forms the plane, the focus of the second lens (including the first lens and the base) for detecting the thermal radiation through the first lens is placed on at least a part of the object to be measured. A typical example will be described. When the plane of the first lens formed by partially cutting a sphere so that the cross section forms the plane and the base in the sample cell are in close contact with each other, a function as a solid immersion lens (an example of the second lens) is exhibited. Therefore, in the method for measuring thermal radiation, thermal radiation of a liquid or an object containing liquid is measured not at the liquid-gas interface, but at the liquid-solid interface. As a result, it is possible to suppress a cooling effect obtained by the heat of vaporization from the object to be measured. Further, the method for measuring thermal radiation detects the thermal radiation through the first lens by allowing one of the object to be measured and the first lens to abut on or separate from the other in the optical axis direction and allowing one of the object to be measured and the first lens to vibrate with respect to the other. Therefore, for example, a signal of thermal radiation (typically, a signal of infrared light) can be measured as a function of the distance between the base in the sample cell and the plane in the first lens. As a result, it becomes possible to observe interference phenomena of infrared light between the base and the plane in the first lens in a condition capable of distinguishing the background radiation and the target signal (thermal radiation) from each other. Further, as described above, in the method for measuring thermal radiation, the base in combination with the first lens exhibits a function as a solid immersion lens (an example of the second lens). Therefore, it is possible to utilize at least a wavelength that is shorter than a wavelength propagating in vacuum or the atmosphere, and therefore improve the space resolution.

Further, in order to prevent unnecessary attenuation of a signal to be measured and exhibit high space resolution, it is preferred that the base and the first lens be each made of a material having a small absorption coefficient and a large dielectric constant in addition to the above method for measuring thermal radiation. Further, design that achieves substantially no spherical aberration when the plane of the first lens formed by partially cutting a sphere so that the cross section forms the plane and the base in the sample cell are in close contact with each other (hereinafter, also referred to as "aplanatic design") further improves the space resolution.

Further, a sample cell for measuring thermal radiation according to an aspect of the present invention is used for detecting thermal radiation of an object to be measured. Specifically, the sample cell for measuring thermal radiation includes the object to be measured which is a liquid or an object containing liquid and a housing part which houses the object to be measured and includes one wall formed of a base transmitting a wavelength of the thermal radiation, and is arranged so that, when the base of the sample cell is in close contact with a plane of a first lens formed by partially cutting a sphere so that the cross section forms the plane, the focus of a second lens is placed on at least a part of the object to be measured located on the base or close to the base, the second lens including the first lens and the base and used for detecting the thermal radiation through the first lens. In addition, the sample cell for measuring thermal radiation is arranged so that one of the object to be measured and the first lens can abut on and separate from the other in the optical axis direction and can vibrate with respect to the other.

In the sample cell for measuring thermal radiation, the sample cell is arranged so that, when the base in the sample cell is in close contact with the plane of the first lens (an objective lens, for example) formed by partially cutting a sphere so that the cross section forms the plane, the focus of the second lens (including the first lens and the base) for detecting the thermal radiation through the first lens is placed on at least a part of the object to be measured. A typical example will be described. When the plane of the first lens formed by partially cutting a sphere so that the cross section forms the plane and the base in the sample cell are in close contact with each other, a function as a solid immersion lens (an example of the second lens) is exhibited. Therefore, in the sample cell for measuring thermal radiation, thermal radiation of a liquid or an object containing liquid is measured not at the liquid-gas interface, but at the liquid-solid interface. As a result, it is possible to suppress a cooling effect obtained by the heat of vaporization from the object to be measured. In addition, the sample cell for measuring thermal radiation is arranged so that one of the object to be measured and the first lens can abut on and separate from the other in the optical axis direction and can vibrate with respect to the other. Therefore, for example, when detecting the thermal radiation through the first lens, a signal of thermal radiation (typically, a signal of infrared light) can be measured as a function of the distance between the base in the sample cell and the plane in the first lens. As a result, it becomes possible to observe interference phenomena of infrared light between the base and the plane in the first lens in a condition capable of distinguishing the background radiation and the target signal (thermal radiation) from each other.

Further, in order to prevent unnecessary attenuation of a signal to be measured and exhibit high space resolution, it is preferred that the base be made of a material having a small absorption coefficient and a large dielectric constant in addition to the above configuration of the sample cell for measuring thermal radiation.

Effects of the Invention

In the apparatus for measuring the characteristic of an object to be measured according to an aspect of the present invention or the method for measuring thermal radiation of an object to be measured according to an aspect of the present invention, for example, a signal of thermal radiation from an object to be measured which is a liquid or an object containing liquid can be measured as a function of the distance between the base of the sample cell, the base forming one wall of the housing part which houses the object to be measured and transmitting a wavelength of the thermal radiation, and the plane in the first lens formed by partially cutting sphere so that the cross section forms the plane. As a result, it becomes possible to observe interference phenomena of infrared light between the base and the plane in the first lens in a condition capable of distinguishing the background radiation and the target signal (thermal radiation) from each other. Further, in the apparatus for measuring the characteristic of an object to be measured according to an aspect of the present invention or the method for measuring thermal radiation of an object to be measured according to an aspect of the present invention, it is possible to utilize at least a wavelength that is shorter than a wavelength propagating in vacuum or the atmosphere, and therefore improve the space resolution.

Further, in the cell for measuring thermal radiation according to an aspect of the present invention, for example, when detecting thermal radiation from an object to be measured which is a liquid or an object containing liquid through the first lens formed by partially cutting sphere so that the cross section forms a plane, a signal of the thermal radiation can be measured as a function of the distance between the base of the sample cell, the base forming one wall of the housing part which houses the object to be measured and transmitting a wavelength of the thermal radiation, and the plane in the first lens. As a result, it becomes possible to observe interference phenomena of infrared light between the base and the plane in the first lens in a condition capable of distinguishing the background radiation and the target signal (thermal radiation) from each other.

Figure 1:
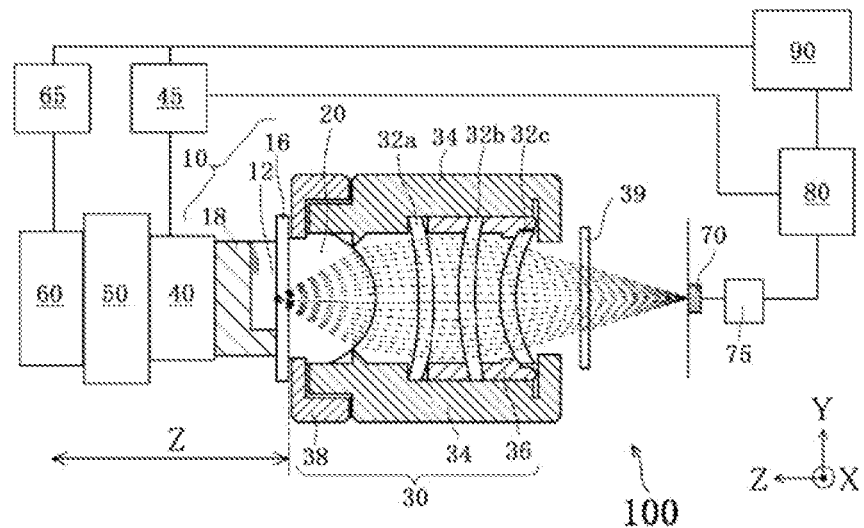
FIG. 1 is a schematic configuration diagram of one mode of an apparatus for measuring thermal radiation of an object to be measured in a first embodiment of the present invention.

DESCRIPTION OF REFERENCE SIGNS 10, 210, 310 sample cell
12, 212, 312 object to be measured
16 base
18 protective cover
20 objective lens
30 lens holder
32a lens
32a each lens
34 outer lens holder
36 inner lens holder
38 outer lens holder
39 detector window
40 vibrational controller
45 function generator
50 parallelism adjuster
52 oblique stage
54a, 54b micrometer
60 position controller
65 stage controller
70 detector
75 preamplifier (low-noise pre-amplifier)
80 lock-in amplifier
90 computer
100, 200, 300 apparatus for measuring thermal radiation of object to be measured
314 culture solution

EMBODIMENTS OF THE INVENTION

Embodiments of the present invention will be described in detail with reference to the accompanying drawings. In the following description, like parts are designated by like reference numerals throughout the drawings. Further, in the drawings, elements of the present embodiment are not necessarily illustrated to follow their scales.

<First Embodiment>

Figure 2:
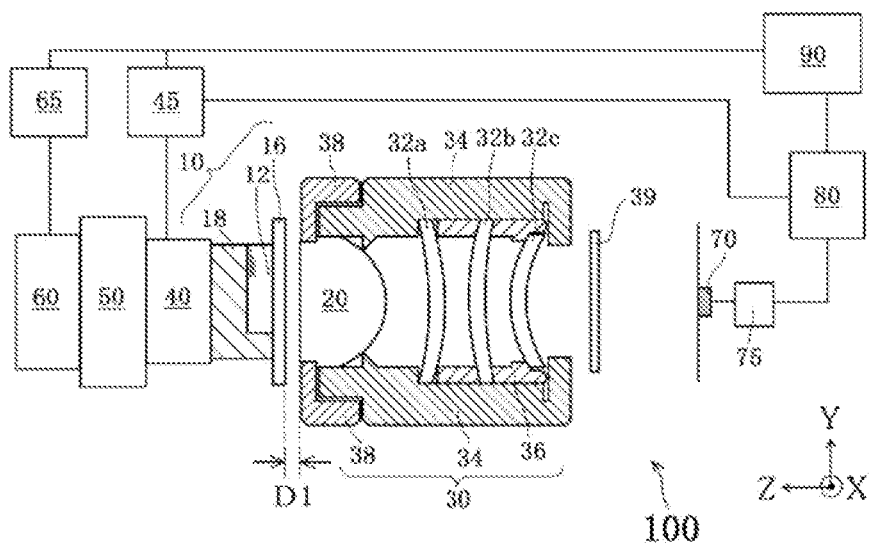
FIG. 2 is a schematic configuration diagram of another mode of the apparatus for measuring thermal radiation of the object to be measured in the first embodiment of the present invention.
Figure 3:
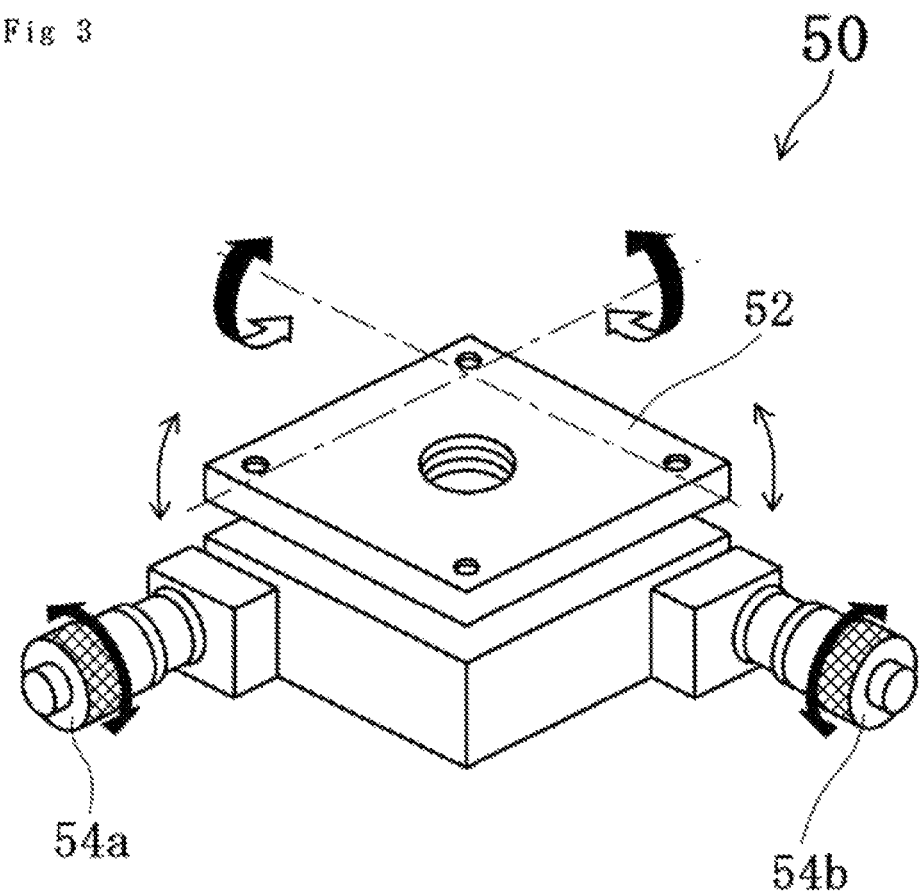
FIG. 3 is a schematic configuration diagram of a parallelism adjuster of the apparatus for measuring thermal radiation of the object to be measured in the first embodiment of the present invention.

FIG. 1 is a schematic configuration diagram of one mode in an apparatus 100 for measuring thermal radiation of an object to be measured (hereinafter, also simply referred to as "the apparatus 100 for measuring thermal radiation") in the present embodiment. FIG. 2 is a schematic configuration diagram of another mode in the apparatus 100 for measuring thermal radiation. The difference between FIG. 1 and FIG. 2 is whether a base 16 of a sample cell 10 is in contact with a surface of an objective lens 20 (an example of a first lens). Because FIG. 1 is a schematic view, a holder which holds each component and a peripheral apparatus or a device such as a cooling apparatus (described later) are omitted in FIG. 1. Further, FIG. 3 is a schematic configuration diagram of a parallelism adjuster 50 which constitutes a part of the apparatus 100 for measuring thermal radiation in the present embodiment.

As illustrated in FIG. 1, the apparatus 100 for measuring thermal radiation of the present embodiment is roughly classified into three component parts.

First, one of the component parts includes the sample cell 10, a vibrational controller 40, the parallelism adjuster 50, and a position controller 60. Further, both the position controller 60 and the vibrational controller 40 of the present embodiment are connected to a computer 90 for monitoring or integrally controlling processing performed by the position controller 60 and the vibrational controller 40. More specifically, the vibrational controller 40 is controlled by a function generator 45 which receives a control signal from the computer 90. The position controller 60 is controlled by a stage controller 65 which receives a control signal from the computer 90.

The vibrational controller 40 of the present embodiment causes the sample cell 10 (more specifically, an object 12 to be measured) to vibrate using a piezoelectric element and controls the frequency of the vibration. For example, the vibrational controller 40 of the present embodiment applies vibration of minute amplitude (approximately 1 μm) to the sample cell 10 at approximately 30 Hz in the optical axis direction (the Z direction in FIGS. 1 and 2).

As illustrated in FIG. 2, the position controller 60 of the present embodiment, for example, controls the sample cell 10 using a piezo-driven stage so that the sample cell 10 can abut on and separate from the below-described objective lens 20 in the optical axis direction. FIG. 2 illustrates a state in which the sample cell 10 is separated from the objective lens 20 by a distance D1.

The parallelism adjuster 50 of the present embodiment is used for correcting the parallelism between the sample cell 10 and the objective lens 20 by measuring the inclination of the sample cell 10 (more specifically, the base 16) relative to a direction of the optical axis of the objective lens 20. As illustrated in FIG. 3, the parallelism adjuster 50 can finely change the angle of an oblique stage 52 using micrometers 54a, 54b.

The object 12 to be measured of the present embodiment is water. The object 12 to be measured is housed inside a housing part which is configured by the base 16 formed of a plate-like germanium (Ge) substrate and a protective cover 18 made of polydimethylsiloxane (abbreviated as PDMS). Therefore, in the present embodiment, the base 16 which transmits the wavelength of thermal radiation serves as one wall of the housing part.

In the present embodiment, the object 12 to be measured is not limited to water that is in contact with the base 16 inside the housing part, that is, water located at the interface between water and the base 16. For example, water that is not in contact with the base 16, but located close to the base 16 can also be the object to be measured in the present embodiment. Therefore, it is only required that the sample cell 10 be arranged so that the focus of the objective lens 20 for detecting thermal radiation from the object 12 to be measured through the objective lens 20 is placed on at least a part of the object 12 to be measured. A method for manufacturing the sample cell 10 is as follows.

Figure 4:
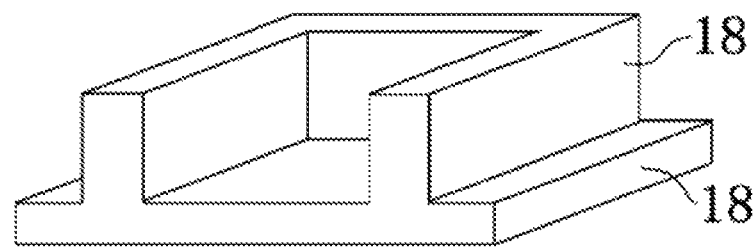
FIGS. 4(a) and 4(b) are cross-sectional views each illustrating a process in steps for manufacturing a sample cell for measuring the object to be measured in the first embodiment of the present invention.
Figure 4:
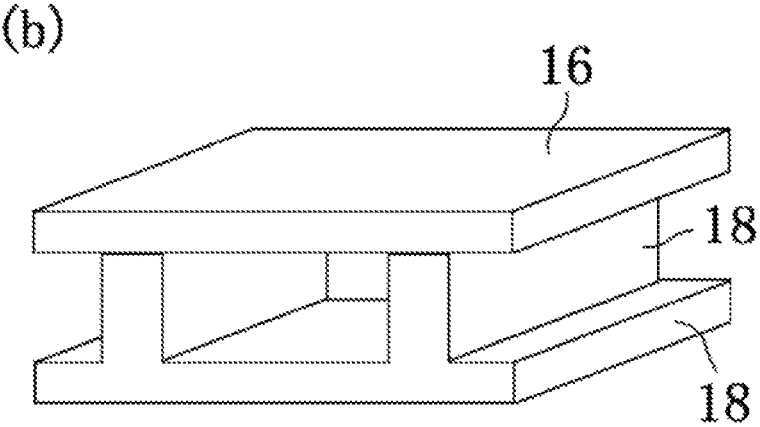

FIGS. 4(a) and 4(b) are cross-sectional views each illustrating a process in steps for manufacturing the sample cell 10 for measuring the object 12 to be measured in the present embodiment. First, PDMS is applied onto glass and left to stand under normal temperature for approximately one day, to thereby cure the PDMS. Then, as illustrated in FIG. 4(a), the PDMS is shaped to produce the protective cover 18. Further, as illustrated in FIG. 4(b), the base 16 is bonded to the PDMS as the protective cover 18 so as to form one surface of the housing part.

PDMS is a material that is compatible with a living body, and therefore has, for example, a property of having less influence on a cell and a tissue. Further, PDMS is a material in which an etching treatment for processing and high-temperature heating for bonding the PDMS to another material are not required and fine shaping can be easily performed. Therefore, PDMS is suitable for the apparatus 100 for measuring thermal radiation of the present embodiment.

In the present embodiment, the objective lens 20 is fixed, and the sample cell 10 is controlled so that the sample cell 10 can abut on and separate from the objective lens 20 in the optical axis direction. However, the present embodiment is not limited to this mode. For example, it is also another employable mode that the sample cell 10 is fixed, and the objective lens 20 (a lens holder 30 which holds the objective lens 20, for example) is controlled so that the objective lens 20 can abut on and separate from the sample cell 10 in the optical axis direction. Further, it is also another employable mode that the objective lens 20 is caused to vibrate instead of the sample cell 10.

Next, the second component part includes the objective lens 20 which mainly captures light caused by thermal radiation of infrared light from the object 12 to be measured (hereinafter, referred to as "thermal radiation light" for the sake of convenience) and a plurality of lenses 32a, 32b, 32c for condensing thermal radiation light passed through the objective lens 20 on a below-described detector 70. For convenience of description, a path of thermal radiation light from the object 12 to be measured is indicated by broken lines in FIG. 1.

The objective lens 20 of the present embodiment is formed by partially cutting a sphere so that the cross section forms a plane, and made of germanium (Ge, the refractive index thereof is approximately 4) having a large dielectric constant (that is, large refractive index). In particular, germanium as the base 16 of the present embodiment has extremely small absorption and is therefore suitable for measuring thermal radiation in the present embodiment. Specifically, for example, the absorption of a germanium substrate having a thickness of 0.4 mm is 5% or less. Further, in the present embodiment, when the base 16 of the sample cell 10 is in close contact with the plane of the objective lens 20 as illustrated in FIG. 1, a function as a solid immersion lens is exhibited. Therefore, the apparatus 100 for measuring thermal radiation of an object to be measured of the present embodiment is configured so that, when the base 16 is in close contact with the plane of the objective lens 20, the focus of a compound lens which is formed of the objective lens 20 and the base 16 for detecting thermal radiation from the object 12 to be measured through the objective lens 20 is placed on at least a part of the object 12 to be measured.

In the present embodiment, the base 16 and the objective lens 20 each made of germanium (Ge) are employed. However, it is also another employable mode that the base 16 which is made of silicon (Si) having a small absorption coefficient and a large dielectric constant and/or the objective lens 20 which is made of silicon (Si) having a small absorption coefficient and a large dielectric constant is employed. Therefore, the objective lens 20 and the base 16 may be made of different materials as long as, when the base 16 of the sample cell 10 is in close contact with the plane of the objective lens 20 as illustrated in FIG. 1, the above-mentioned compound lens for detecting thermal radiation from the object 12 to be measured through the objective lens 20 comes into focus. However, in view of easiness of design of the optical system, the objective lens 20 and the base 16 are preferably made of the same material.

In the present embodiment, the base 16 and the objective lens 20 each made of germanium (Ge) are employed as described above, which brings an advantage such that a wavelength range of the maximum sensitivity of the below-described detector 70 (mid-infrared light) is not absorbed or not likely to be absorbed. In addition, high space resolution, to be described below, is exhibited by the employment of the base 16 and the objective lens 20 each made of germanium (Ge).

The plurality of lenses 32a, 32b, 32c of the present embodiment are meniscus lenses made of germanium (Ge) and held by a first outer lens holder 34 and an inner lens holder 36 of a lens holder 30. Further, the objective lens 20 is held by the first outer lens holder 34 and a second outer lens holder 38 of the lens holder 30. In the present embodiment, the objective lens 20 and the lenses 32a, 32b, 32c each made of germanium (Ge) are employed, which brings an advantage such that the wavelength range of the maximum sensitivity of the below-described detector 70 (mid-infrared light) is not absorbed or not likely to be absorbed. In addition, high space resolution, to be described below, is exhibited because of the employment of the objective lens 20 and the lenses 32a, 32b, 32c each made of germanium (Ge).

Further, antireflection films are applied to the objective lens 20 and the lenses 32a. 32b, 32c of the present embodiment in order to increase the transmittance of light having a wavelength of approximately 10 μm. In the present embodiment, the objective lens 20 and the lenses 32a, 32b, 32c each made of germanium (Ge) are employed. However, it is also another employable mode that the objective lens 20 made of silicon (Si) having a small absorption coefficient and a large dielectric constant and/or the lenses 32a, 32b, 32c made of silicon (Si) having a small absorption coefficient and a large dielectric constant are employed. In view of the easiness of design of the optical system or more accurately designing aplanatic lenses, the objective lens 20 and the lenses 32a, 32b, 32c are preferably formed of the same material. In particular, in the present embodiment, in order to more accurately design aplanatic lenses, a curved surface of the lens 32a which is located closest to the objective lens 20, the curved surface facing the objective lens 20, is allowed to have substantially no spherical aberration by achieving the same relationship as illustrated in FIG. 5, which will be described below.

In addition, in the present embodiment, the apparatus 100 for measuring thermal radiation is configured so that, when the base 16 of the sample cell 10 is in close contact with the plane of the objective lens 20, the above-mentioned compound lens for detecting thermal radiation comes into focus while achieving the aplanatic lens design. Therefore, it should be especially noted that, in the method for measuring thermal radiation, thermal radiation of a liquid or an object containing liquid is measured not at the liquid-gas interface, but at the liquid-solid interface, and it is therefore possible to suppress a cooling effect obtained by the heat of vaporization from the object to be measured.

Figure 5:
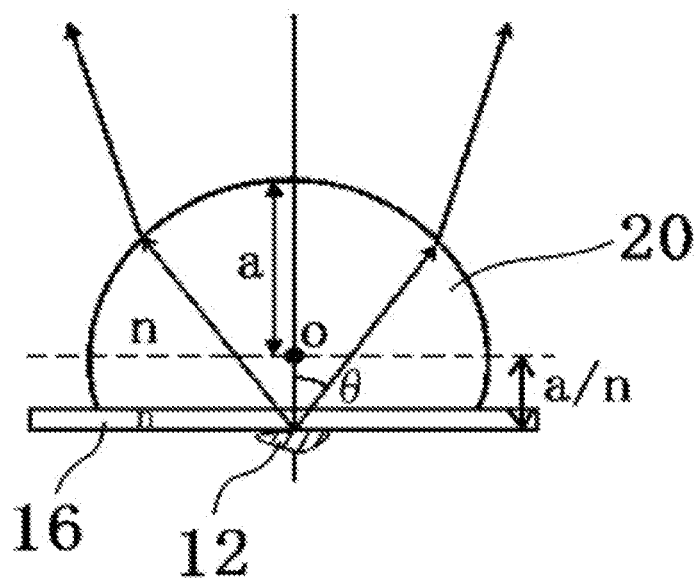
FIG. 5 is a diagram illustrating the relationship between an objective lens designed as an aplanatic lens and a base in the first embodiment of the present invention.

FIG. 5 is a diagram illustrating the relationship between the objective lens 20 designed as an aplanatic lens and the base 16 in the present embodiment. As illustrated in FIG. 5, in the present embodiment, a value (a/n) obtained by dividing the radius (a in FIG. 5) of a sphere of a superhemisphere lens which is formed by the objective lens 20 and the base 16 by the refractive index (n in FIG. 5) of the objective lens 20 and the base 16 is approximately equal to the distance between the center of the sphere (o in FIG. 5) and the interface between the object 12 to be measured and the base 16. In the apparatus 100 for measuring thermal radiation of the present embodiment in which the aplanatic lenses are designed, an effect of preventing defocus can be achieved, for example, even when a value of θ in FIG. 5 is increased. Increasing a value of θ makes it possible to obtain thermal radiation at a focal position over a wide radiation angle. Therefore, a "lighter" optical system is realized.

Therefore, the space resolution (ΔX) based on the Rayleigh criterion is calculated using the following formula.

$$\Delta X = 0.61 \times \frac{\lambda}{n \sin\theta} \quad \text{[Formula 1]}$$

As represented by Formula 1, as the value of θ increases, the space resolution also increases. Therefore, the apparatus 100 for measuring thermal radiation of the present embodiment in which the aplanatic lenses are designed is a preferred mode. In the present embodiment, λ is approximately 10 μm, n is the refractive index (4.005) of germanium which constitutes the objective lens 20 and the base 16, and θ is 38.7°. As a result, the space resolution (ΔX) of the present embodiment is approximately 2.5 μm, and therefore extremely high.

In this application. "substantially" in the description "design is made so as to have substantially no spherical aberration" is an expression taking into consideration the difference between mathematically no spherical aberration and spherical aberration that is actually measured. More specifically, when the objective lens 20 is arranged at an accurate position as illustrated in FIG. 5, there is no spherical aberration mathematically. However, for example, the processing accuracy or the alignment accuracy of a lens is rarely perfect. Therefore, the expression "substantially" may include an error in the range of spherical aberration that may be left under a real measurement environment taking the above into consideration.

Further, the third component part of the apparatus 100 for measuring thermal radiation of the present embodiment includes the detector 70 for detecting the condensed thermal radiation light described above, a preamplifier (low-noise pre-amplifier) 75 which amplifies the detected light, and a lock-in amplifier 80 which receives a reference signal from the function generator 45 and extracts a signal as an object to be measured from the amplified light. The lock-in amplifier 80 is connected to the computer 90 for monitoring or integrally controlling the processing of the lock-in amplifier 80.

The detector 70 of the present embodiment is provided with a mercury cadmium telluride (HgCdTe) high-sensitivity photoconductive element manufactured by Hamamatsu Photonics K.K. Therefore, as illustrated in FIG. 1, in order to allow the detector 70 to operate under the temperature condition of 77K, a window 39 which is made of zinc sulfide (ZnS) is provided for vacuum insulation from room temperature. The wavelength of the maximum sensitivity of the detector 70 is approximately 10.3 μm (mid-infrared light). Further, in the present embodiment, the area of a focal spot of the detector 70 is approximately 625 μm2 (approximately 25 μm×approximately 25 μm). In the present embodiment, the size of the focus of the thermal radiation light that enters the detector 70 is substantially equal to the light receiving area of the detector 70 (the area of a circle having a diameter of 37.7 μm, for example). Therefore, higher detection sensitivity and higher space resolution may be achieved.

Further, the detector 70 detects not only a target signal from the object 12 to be measured (more specifically, a signal of thermal radiation light), but also a signal of thermal radiation light (background radiation light) from an object other than the object to be measured. Therefore, in the present embodiment, when vibration of minute amplitude (approximately 1 μm) is applied to the object 12 to be measured, for example, in the optical axis direction at a frequency of 26.8 Hz using the vibrational controller 40, the target signal can be measured by extracting only a signal of thermal radiation light, the signal being modulated with a frequency of 26.8 Hz, using the lock-in amplifier 80.

<Preliminary Experiment in Thermal Radiation Measurement>

FIG. 6(a) is a conceptual diagram explaining the interference of thermal radiation from the object 12 to be measured in the present embodiment. FIG. 6(b) is an explanatory diagram of the expected intensity distribution of interference light of thermal radiation from the object 12 to be measured (upper graph) and a signal when the thermal radiation is detected by the lock-in amplifier 80 (lower graph) in the present embodiment.

As described above, the apparatus 100 for measuring thermal radiation of the present embodiment changes the distance in the Z direction illustrated in FIG. 6(a) using the position controller 60 while applying minute vibration to the sample cell 10 (specifically, the object 12 to be measured) using the vibrational controller 40. In the present embodiment, the refractive index of the objective lens 20 is approximately 4, and the refractive index in the atmosphere is approximately 1. Therefore, as illustrated in FIG. 6(a), in thermal radiation light (mainly, infrared light) from the object 12 to be measured, the interference occurs between light that directly reaches the detector 70 through the objective lens 20 and light that reaches the detector 70 after being fixed-end reflected between the base 16 and the objective lens 20. In this case, the upper graph of FIG. 6(b) is expected to appear by taking into consideration a condition of strengthening light and a condition of weakening light by the interference (FIG. 6(a)).

Further, a differential amount of the interference intensity of thermal radiation (that is, dI/dz) can be obtained using the lock-in amplifier 80 of the present embodiment as illustrated in the lower graph of FIG. 6(b).

The inventor of this application measured, as a preliminary experiment, a target signal that is extracted using the lock-in amplifier 80 of the present embodiment (that is, a signal of interference light of thermal radiation of water) when water is employed as the object 12 to be measured and vibration of minute amplitude (approximately 1 μm) is applied to the object 12 to be measured in the optical axis direction at a frequency of 26.8 Hz.

Figure 6:
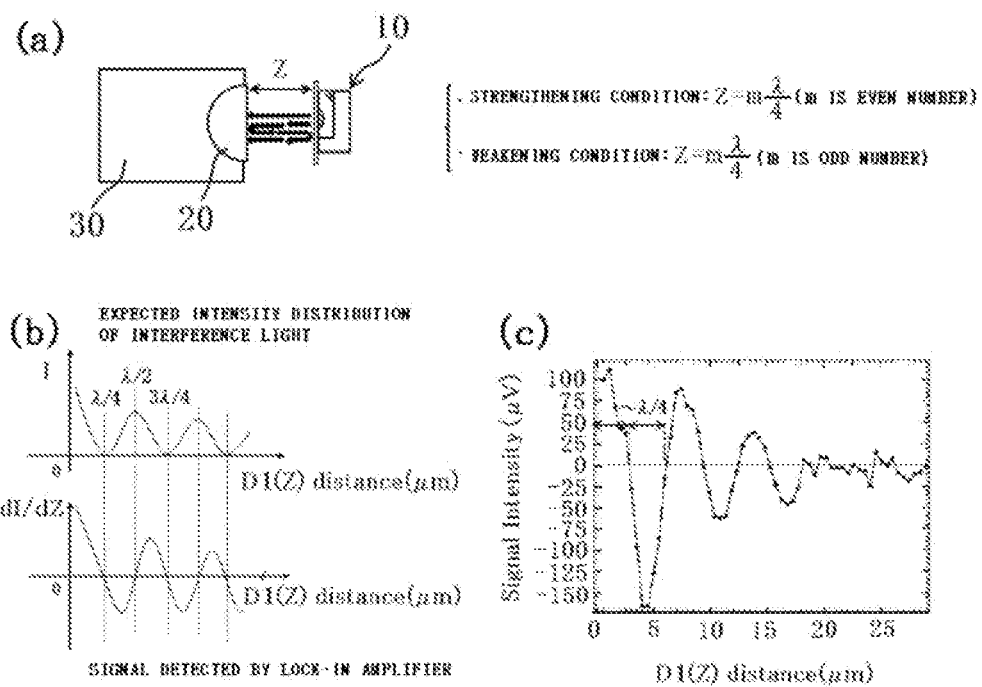
FIG. 6(a) is a conceptual diagram explaining the interference of thermal radiation from the object to be measured in the first embodiment of the present invention.
FIG. 6(b) is an explanatory diagram of the expected intensity distribution of interference light of thermal radiation from the object to be measured (upper graph) and a signal when the thermal radiation is detected by a lock-in amplifier in the first embodiment of the present invention.
FIG. 6(c) is a graph illustrating the relationship between the distance and the intensity of thermal radiation of the object to be measured (water) in a preliminary experiment of the first embodiment of the present invention.

FIG. 6(c) is a graph illustrating the relationship between the distance and the intensity of thermal radiation of the object 12 to be measured (water) in the preliminary experiment of the present embodiment. As illustrated in FIG. 6(c), it has been confirmed that the target signal extracted using the lock-in amplifier 80 of the present embodiment substantially coincides with the lower graph of FIG. 6(*b*).

<Adjustment of Parallelism>

When measuring thermal radiation from the object 12 to be measured using the apparatus 100 for measuring thermal radiation of the present embodiment, it is preferred to increase the parallelism between the base 16 and the objective lens 20 as much as possible. When high parallelism is achieved, it is possible to cause vibration with the distance between the base 16 (specifically, the object 12 to be measured) and the objective lens 20 made small.

Figure 7:
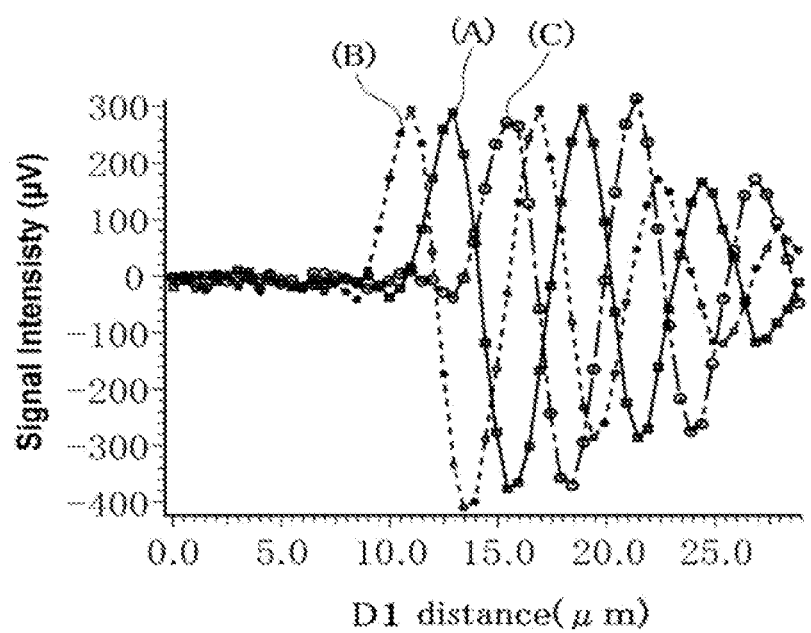
FIG. 7 is a graph illustrating a result of measurement obtained by measuring, at different positions, a differential amount of the interference intensity of thermal radiation from the object to be measured (water) with respect to the distance between the base 16 and the objective lens 20 before adjusting the parallelism in the first embodiment of the present invention.

FIG. 7 is a graph illustrating a result of measurement obtained by measuring, at different positions, a differential amount of the interference intensity of thermal radiation of the object 12 to be measured with respect to the distance between the base 16 and the objective lens 20 before adjusting the parallelism by the parallelism adjuster 50 in the present embodiment. In the present embodiment, the object 12 to be measured used for adjusting the parallelism is water.

Specifically, a graph (A) of FIG. 7 shows a differential amount of the interference intensity of thermal radiation measured using the apparatus 100 for measuring thermal radiation of the present embodiment when the sample cell 10 is arranged at a reference position. A graph (B) of FIG. 7 shows a differential amount of the interference intensity of thermal radiation measured when the sample cell 10 is moved to a direction perpendicular to the plane of FIG. 1 (X direction) from the reference position of the graph (A) by 200 μm. Further, a graph (C) of FIG. 7 shows a differential amount of the interference intensity of thermal radiation measured when the sample cell 10 is moved to a direction perpendicular to the plane of FIG. 1 (X direction) as well as opposite to the direction of the graph (B) from the reference position of the graph (A) by 200 μm.

As illustrated in FIG. 7, before the parallelism between the base 16 and the objective lens 20 is adjusted, a peak position of the interference intensity of thermal radiation is shifted by approximately 2 μm response to the movement by 200 μm of the sample cell 10 in the X direction illustrated in FIG. 1.

$$\tan^{-1}\frac{2}{200} \approx 0.3° \quad \text{[Formula 2]}$$

As a result, the above calculation formula shows that the base 16 is inclined by approximately 0.3° relative to the optical axis direction. In other words, the parallelism between the base 16 and the objective lens 20 is approximately 0.3°.

As described above, the inclination of the base 16 relative to the optical axis direction can be measured with extremely high accuracy by measuring a differential amount of the interference intensity of thermal radiation of the object 12 to be measured with respect to the distance between the base 16 and the objective lens 20 at a plurality of different positions in the sample cell 10. As a result, it is possible to correct the parallelism between the base 16 and the plane of the objective lens 20 with high accuracy by repeatedly performing an operation of adjusting the inclination of the base 16 using the parallelism adjuster 50 and the above operation of measuring a differential amount of the interference intensity of thermal radiation of the object 12 to be measured at a plurality of different positions in the sample cell 10.

It has been confirmed that the parallelism of the apparatus 100 for measuring thermal radiation of the present embodiment falls within ±0.06° or less by performing the above operations. Therefore, it should be especially noted that the present embodiment makes it possible to achieve the parallelism that can be higher than the parallelism achieved by the existing technique (representatively, the parallelism obtained by using a known CCD microscope or the like) in a state in which the components of the apparatus 100 for measuring thermal radiation have been set, for example, immediately before starting the actual measurement. More specifically, in controlling the distance between the base 16 and the objective lens 20, when the distance becomes approximately 1 μm, it is not possible to ignore variations in the components caused by thermal expansion or shrinkage due to a change in the temperature of a room in which the apparatus 100 for measuring thermal radiation is placed. Therefore, the present embodiment makes it possible to easily confirm the parallelism appropriately depending on the measurement environment or measurement condition. Although there has been described the parallelism measured regarding the X direction in FIG. 1 in the above example of the adjustment of the parallelism, the parallelism can be adjusted also regarding the Y direction in FIG. 1 in the same manner as the X direction.

Therefore, it is a preferred mode that the inclination of the base 16 relative to the optical axis, the inclination being obtained by measuring the interference between thermal radiation of the object 12 to be measured and thermal radiation that occurs when the thermal radiation of the object 12 is reflected by the plane of the objective lens 20 and the base 16 and then enters the objective lens 20, is measured before detecting or measuring the thermal radiation from the object 12 to be measured, to thereby correct the parallelism between the base 16 and the plane of the objective lens 20.

In the present embodiment, after correcting the parallelism, a step for bringing the base 16 close to the objective lens 20 is performed based on the distance between the base 16 and plane of the objective lens 20 obtained by the above measurement of the interference before detecting or measuring thermal radiation from the object 12 to be measured. As a result, it is possible to allow the base 16 (specifically, the object 12 to be measured) to minutely vibrate while reducing the distance between the base 16 and the objective lens 20 as much as possible.

EXAMPLE

Next, there was performed an experiment using the apparatus 100 for measuring thermal radiation of the first embodiment for confirming that thermal radiation from the surface of the base 16, that is, the object 12 to be measured can be clearly distinguished from thermal radiation from the peripheral environment including an object to be measured for reference (PDMS).

Figure 8:
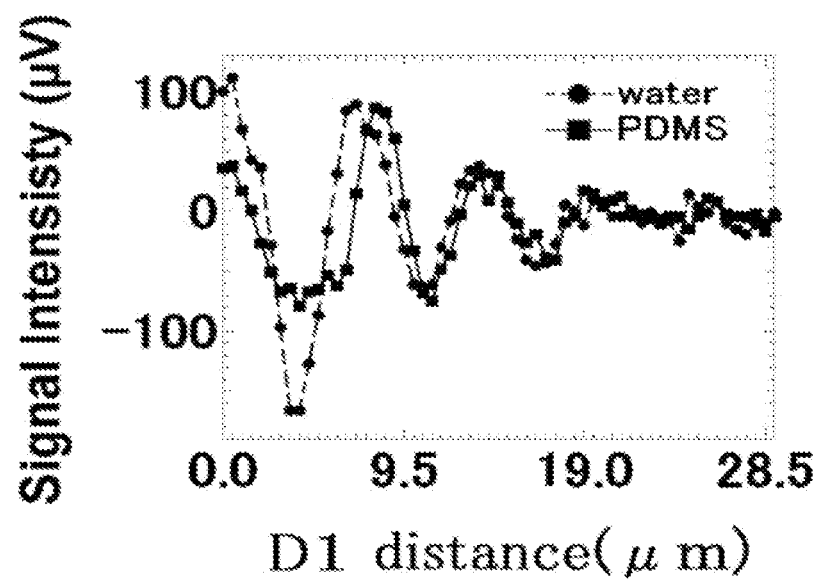
FIG. 8 is a graph illustrating the difference in the interference intensity of thermal radiation between the object to be measured (water) and an object to be measured for reference (PDMS) with respect to the distance in the first embodiment of the present invention.

FIG. 8 is a graph illustrating the difference in the interference intensity of thermal radiation between the object to be measured and the object to be measured for reference with respect to the distance in the example. In the example, water was used as the object 12 to be measured, and PDMS was used as the object to be measured which emits background radiation. Further, in the example, a differential amount of the interference intensity of thermal radiation from the sample cell 10 with respect to the distance between the base 16 and the objective lens 20 after adjusting the parallelism by the parallelism adjuster 50 in the first embodiment was measured at different positions. In addition, in the example, the measurement was performed while applying vibration of minute amplitude (approximately 1 μm) to the object 12 to be measured in the optical axis direction at a frequency of 26.8 Hz, for example.

As a result, as illustrated in FIG. 8, it has been confirmed that, in an area in which the sample cell 10 and the objective lens 20 are located close to each other (for example, the distance D1 in FIG. 2 is 1 µm or less), the intensity of a signal when the focus thereof is placed on the object 12 to be measured (water) is approximately three times as large as the intensity of a signal when the focus thereof is placed on the object to be measured for reference (PDMS). Because the entire sample cell 10 is in a thermal equilibrium state, the above phenomenon can be considered as not reflecting a difference in temperature, but distinguishing a difference in thermal radiation caused by a difference in radiation efficiency specific to a substance. Therefore, it has been confirmed by the example that the thermal radiation from the surface of the base 16 (that is, the object 12 to be measured) can be clearly distinguished from the thermal radiation from the peripheral environment including the object to be measured for reference (PDMS).

As described above, the apparatus 100 for measuring thermal radiation of the present embodiment makes it possible to achieve exhibition of high space resolution and/or accurate distinction between background radiation and a target signal in a non-contact and non-destructive manner. In addition, it should be especially noted that a method for previously adjusting the apparatus for measuring thermal radiation for achieving the exhibition of high space resolution and/or the background radiation and the target signal has been successfully found out.

<Another Embodiment>

Figure 9:
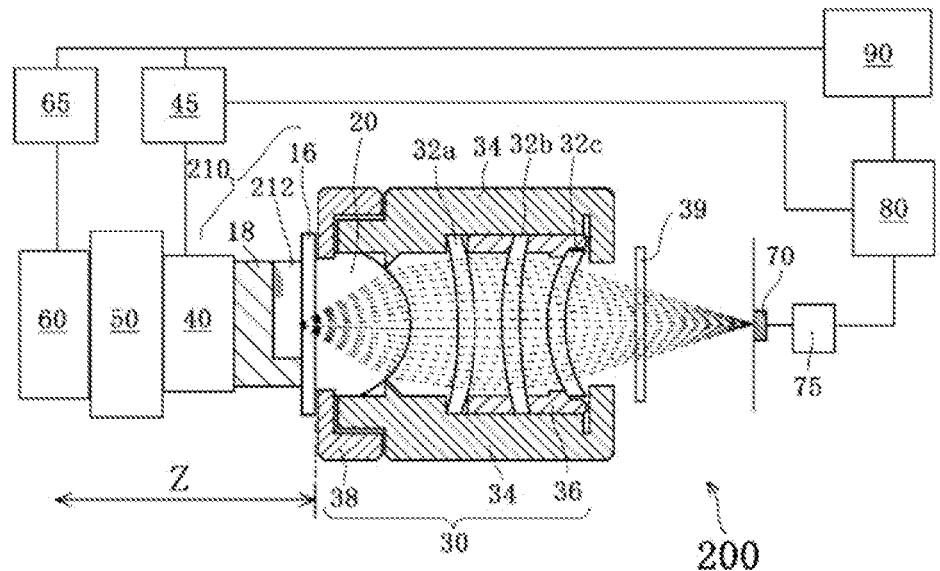
FIG. 9 is a schematic configuration diagram of one mode of an apparatus for measuring thermal radiation of an object to be measured in another embodiment of the present invention.

FIG. 9 is a schematic configuration diagram of an apparatus 200 for measuring thermal radiation of an object to be measured in another embodiment and corresponds to FIG. 1. The apparatus 200 for measuring thermal radiation of the present embodiment is the same as the apparatus 100 for measuring thermal radiation of the first embodiment except for that the sample cell 10 of the first embodiment is modified to a sample cell 210. Therefore, description for overlapping points may be omitted.

In the sample cell 210 of the apparatus 200 for measuring thermal radiation, an object 212 to be measured which includes two kinds of solutions that can chemically react on each other is housed inside a housing part which includes a base 16 and a protective cover 18 made of PDMS. Measuring thermal radiation emitted at the stage of the chemical reaction inside the housing part in time series using a detector 70 as in the present embodiment is also an employable mode. Therefore, even when the object 212 to be measured is composed of only liquid, the same effect as obtained in the first embodiment can be achieved. Further, it is possible to measure the space distribution, that is, the temperature distribution of thermal radiation of liquid adjacent to the base 16 by operating a position controller 60 (a piezo-driven stage in the present embodiment).

Figure 10:
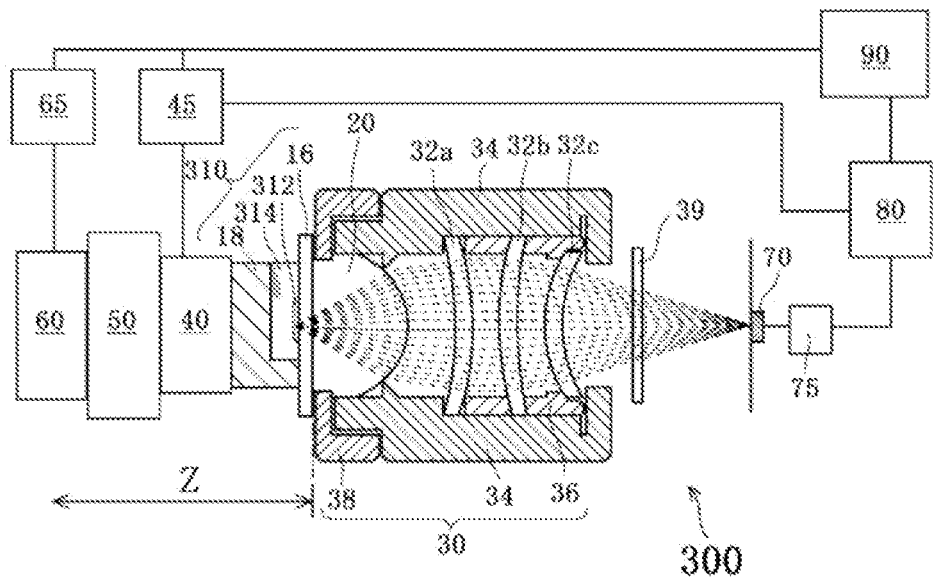
FIG. 10 is a schematic configuration diagram of one mode of an apparatus for measuring thermal radiation of an object to be measured in another embodiment of the present invention.

Further, as another mode, as illustrated in an apparatus 300 for measuring thermal radiation of FIG. 10, a cell (for example, an amoeba proteus or a type of cancer cell (HeLa cell)) inside a sample cell 310 can also be used as an object 312 to be measured instead of the objects 12, 212 to be measured described above. In this case, the object 312 to be measured is cultured in a culture solution 314 which is housed inside a housing part which includes a base 16 and a protective cover 18 made of PDMS. In the present embodiment, a cell as the object 12 to be measured is arranged on the base 16 together with the culture solution 14. Therefore, at the point when the base 16 and the protective cover 18 are bonded to each other, the object 12 to be measured is housed inside the housing part. In the present embodiment, when measuring thermal radiation from the cell as the object 312 to be measured, the cell is allowed to adhere to the base 16, and thermal radiation from the adhered cell is measured thorough the base 16.

Although the cell as the object 312 to be measured is cultured on the base 16 in view of the easiness of culture in the present embodiment, the present embodiment is not limited to the above mode. For example, it is also another employable mode that the object 312 to be measured is arranged not on the base 16, but at a position closer to the base 16 inside the housing part. Therefore, it is only required that the sample cell 10 be arranged so that the focus of the objective lens 20 for detecting thermal radiation from the object 312 to be measured through the objective lens 20 is placed on at least a part of the object 312 to be measured.

Further, although the vibrational controller 40 and the position controller 60 are arranged as separate components in each of the above embodiments, each of the above embodiments is not limited to such a mode. For example, when a piezo-driven stage as a position controller 60 that can vibrate also in the Z direction in FIG. 1 is employed, the vibrational controller 40 and the position controller 60 can be integrated with each other. Therefore, even when such a mode is employed, the same effect as obtained in each of the above embodiments can be achieved.

The disclosure of the above embodiments has been described not for limiting the invention, but for explaining the embodiments. In addition, modifications that fall within the scope of the invention including another combination of the embodiments also fall within the scope of claims.

INDUSTRIAL APPLICABILITY

The apparatus for measuring thermal radiation of an object to be measured, the method for measuring thermal radiation of an object to be measured, and the sample cell for measuring thermal radiation of the present invention make it possible to achieve exhibition of high space resolution and/or accurate distinction between background radiation and a target signal in a non-contact and non-destructive manner when the object to be measured is a liquid or an object containing liquid. Therefore, the apparatus for measuring thermal radiation of the object to be measured, the method for measuring thermal radiation of the object to be measured, and the sample cell for measuring thermal radiation can be widely utilized in various technical fields including a pharmaceutical field, a chemical field, a field of basic research and measuring instrument in life science.

The invention claimed is:

1. An apparatus for measuring thermal radiation of an object, the apparatus comprising:
   a sample cell including:
      a housing for housing the object, the housing including one wall formed of a base capable of transmitting the thermal radiation, the object being a liquid or an object containing a liquid;
      a first lens including plane surface, wherein the sample cell is arranged so that, when the base is in contact with the plane surface of the first lens, focus of a second lens is placed on at least a part of the object at an interface between the object and the base, the second lens consisting of the first lens and the base;

a position controller for controlling position of one of the base and the first lens so as to be able to abut on and separate from the other in an optical axis direction;

a vibrational controller for controlling vibration of one of the base and the first lens to vibrate with respect to the other and controlling a frequency of the vibration;

a detector for detecting the thermal radiation through the first lens; and a parallelism adjuster for correcting parallelism between a plate-like substrate as the base and the plane surface by measuring an inclination of the plate-like substrate relative to an optical axis direction, the inclination being obtained by measuring interference between thermal radiation of the object and thermal radiation that occurs when the thermal radiation of the object is reflected by the plane surface and the plate-like substrate and enters the first lens.

2. The apparatus for measuring thermal radiation of the object according to claim 1, wherein the base is made of a material and the first lens is made from the same material.

3. The apparatus for measuring thermal radiation of the object according to claim 2, wherein, when the base of the sample cell is in contact with the plane surface of the first lens, the second lens for detecting the thermal radiation comes into focus so as to have substantially no spherical aberration.

4. The apparatus for measuring thermal radiation of the object according to claim 1, wherein a size of the focus of light of the thermal radiation is substantially equal to a light receiving area of the detector.

5. The apparatus for measuring thermal radiation of an object according to claim 1, wherein, the focus of the second lens is not on at least a part of the object at the interface between the object and the base when the base is separated from the plane surface of the first lens.

6. The apparatus for measuring thermal radiation of an object according to claim 1, wherein the focus of the second lens is not on the detector when the base is separated from the plane surface of the first lens.

7. A method for measuring thermal radiation of an object, the method comprising the steps of:

preparing a sample cell, the sample cell including the object, the object being a liquid or an object containing liquid and a housing for housing the object and including one wall formed of a base capable of transmitting the thermal radiation, wherein the sample cell is arranged so that, when the base is in contact with a plane surface of a first lens, focus of a second lens is placed on at least a part of the object at an interface between the object and the base, the second lens consisting of the first lens and the base;

detecting the thermal radiation through the first lens using the sample cell by causing one of the object and the first lens to abut on or separate from the other in an optical axis direction and causing one of the object and the first lens to vibrate with respect to the other; and before detecting the thermal radiation, correcting parallelism between a plate-like substrate as the base and the plane surface by measuring an inclination of the plate-like substrate relative to an optical axis direction, the inclination being obtained by measuring interference between thermal radiation of the object and thermal radiation that occurs when the thermal radiation of the object is reflected by the plane surface and the plate-like substrate and enters the first lens.

8. The method for measuring thermal radiation of the object according to claim 7, wherein the base is made of a material and the first lens is made from the same material.

9. The method for measuring thermal radiation of the object according to claim 8, wherein, when the base of the sample cell is in contact with the plane surface of the first lens, the second lens for detecting the thermal radiation comes into focus so as to have substantially no spherical aberration.

10. The method for measuring thermal radiation of the object according to claim 7, further comprising
after the step of correcting the parallelism and before detecting the thermal radiation, a step of bringing the plate-like substrate towards the first lens based on a distance between the plate-like substrate and the plane surface, the distance being obtained by measuring the interference.

11. The method for measuring thermal radiation of an object according to claim 7, wherein, the focus of the second lens is not on at least a part of the object at the interface between the object and the base when the base is separated from the plane surface of the first lens.

12. The method for measuring thermal radiation of an object according to claim 7, wherein the focus of the second lens is not on the detector when the base is separated from the plane surface of the first lens.

13. The method for measuring thermal radiation of the object according to claim 7, further comprising:
after the step of correcting the parallelism and before detecting the thermal radiation, a step of bringing the plate-like substrate towards the first lens based on a distance between the plate-like substrate and the plane surface, the distance being obtained by measuring the interference.

14. A sample cell for measuring thermal radiation, the sample cell being used for detecting thermal radiation of an object, the sample cell comprising:

a housing for housing the object and including one wall formed of a base capable of transmitting the thermal radiation, the object being a liquid or an object containing a liquid, wherein the sample cell is arranged so that, when the base of the sample cell is in contact with a plane surface of a first lens, the focus of a second lens is placed on at least a part of the object at an interface between the object and the base, the second lens consisting of the first lens and the base, and one of the object and the first lens is able to abut on and separate from the other in an optical axis direction and vibrate with respect to the other; and a parallelism adjuster for correcting parallelism between a plate-like substrate as the base and the plane surface by measuring an inclination of the plate-like substrate relative to the optical axis direction, the inclination being obtained by measuring interference between thermal radiation of the object and thermal radiation that occurs when the thermal radiation of the object is reflected by the plane surface and the plate-like substrate and enters the first lens.

15. The sample cell for measuring thermal radiation according to claim 14, wherein the base is made of a material and the first lens is made of the same material.

16. The sample cell for measuring thermal radiation according to claim 14, wherein, the focus of the second lens is not on at least a part of the object at the interface between the object and the base when the base is separated from the plane surface of the first lens.

17. The sample cell for measuring thermal radiation according to claim 14, wherein, the focus of the second lens is not on the detector when the base is separated from the plane surface of the first lens.

\* \* \* \* \*